United States Patent [19]

Hsu et al.

[11] Patent Number: 4,861,896
[45] Date of Patent: Aug. 29, 1989

[54] PREPARATION OF HALO SUBSTITUTED ISOTHIAZOLONES

[75] Inventors: Adam C. T. Hsu, Lansdale; Geore M. Lein, Jr., Chalfont, both of Pa.

[73] Assignee: Rohm and Haas Company, Philadelphia, Pa.

[21] Appl. No.: 112,786

[22] Filed: Oct. 26, 1987

[51] Int. Cl.$^4$ ............................................ C07D 275/02
[52] U.S. Cl. .................................................. 548/213
[58] Field of Search ......................................... 548/213

[56] References Cited

U.S. PATENT DOCUMENTS 3,761,488  9/1973  Lewis et al. ........................ 548/213
3,914,301 10/1975  Miller et al. ....................... 548/213

FOREIGN PATENT DOCUMENTS 95907 12/1983 European Pat. Off. .

OTHER PUBLICATIONS

Tetrahedron Letters 42, 3719 (1970), Nakagawa et al.
Leonard et al., Tetrahedron Letters, No. 23, pp. 1471–1475 (1964).

Primary Examiner—Anton H. Sutto
Assistant Examiner—Diana G. Rivers
Attorney, Agent, or Firm—Michael B. Fein; Terance P. Strobaugh

[57] ABSTRACT

This invention relates to an improved preparation of halo substituted isothiazolones by a single-step synthesis. The products are useful as biocides.

11 Claims, No Drawings

PREPARATION OF HALO SUBSTITUTED ISOTHIAZOLONES

2-Substituted isothiazolones, 4-halo-, 5-halo-, and 4,5-dihaloisothiazolones are well-known as useful chemicals for the control of living organisms, especially as biocides. Routes to the manufacture of these materials have been described in U.S. Pat. No. 3,761,488 and European Patent Publication No.95907. These preparations may require several preparative steps, involving costly or difficultly obtainable intermediates.

U.S. Ser. No. 892,961 filed 8/4/86 discloses preparing substituted acrylamides useful in the present process; however, the substituted acrylamide is reacted with a thiolating agent, to form the 3-mercaptopropionamide, then in a separate step is reacted with chlorine to close the ring to form the appropriate isothiazolone.

Nagagawa et al. [Tetrahedron Letters, 42, 3719 (1970)] teach the direct reaction of a halogenating agent, such as sulfur monochloride, sulfur dichloride, or thionyl chloride, with acrylonitrile or crotonitrile to form the 3,4-dichloro-5-substituted-isothiazole. However, no reaction with an acrylamide derivative is taught or suggested; moreover, the resulting di- or trihaloisothiazole requires an additional step to convert it to the desired isothiazolone.

We have discovered a new preparation of halo substituent isothiazolones (I, infra) by a single-step synthesis from an N-substituted acrylamide or 2-haloacrylamide (II, infra), and a sulfur halide (III,infra) for example $SCl_{+2}$ or $S_2$ optionally with an organic base.

The following equation illustrates this process.

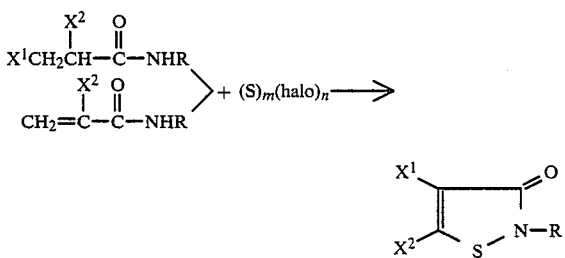

wherein
$X^1$ is halo such as bromo, chloro and the like; $X^2$ is hydrogen or halo, such as bromo, chloro and the like; and
R is alkyl of from 1 to 18 carbon atoms, alkenyl or alkynl of from 2 to 18 carbon atoms, and preferably from 2 to 4 carbon atoms, a cycloalkyl of from 3 to 12 nuclear carbon atoms, preferably from 3 to 8 nuclear carbon atoms, aralkyl of from up to 10 carbon atoms, or aryl of up to 10 carbon atoms; and m and n are integers of 1 or 2.

As used in the specification and claims, the term "alkyl" is intended to include unsubstituted alkyls as well as substituted alkyls in which one or more of the hydrogen atoms are replaced by another substituent. Examples of substituted alkyl include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, isothiazolonylalkyl, haloalkoxyalkyl, carbamoxyalkyl, azacycloalkylalkyl, such as morpholinoalkyl, piperdinoalkyl, pyrrolidonylalkyl, and the like. The terms "alkenyl" and "alkynyl" include substituted and unsubstituted alkenyls and alkynyls such as haloalkenyl, haloalkynyl, and the like.

The term "aralkyl" includes substituted and unsubstituted aralkyls having one or more of the hydrogen atoms on either the aryl ring or the alkyl chain replaced by another substituent. Examples of the substituted aralkyls include halogen-, nitro-, $(C_1-C_4)$alkyl-, or $(C_1-C_4)$alkoxy-substituted aralkyls, and the like.

The term "aryl" includes substituted and unsubstituted aryls, such as phenyl, naphthyl, or pyridyl, as well as aryls having one or more of the hydrogen atoms on the aryl ring replaced by another substituent such as halo, cyano, nitro, $(C_1-C_4)$alkyl, $(C_1-C_4)$alkoxy, $(C_1-C_4)$alkylacylamino, $(C_1-C_4)$carbalkoxy, sulfamyl, and the like.

Representative R substituents include methyl, ethyl, propyl, isopropyl, butyl, hexyl, octyl, decyl, pentadecyl, octadecyl, cyclopropyl, cyclohexyl, cyclo octyl benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, p-chloroanilinomethyl, phenylcarbamoxymethyl, hydroxybutyl, allyl, propynyl, vinyl, carboxyethyl, 1-isothiazolonylethyl, 1,2,2-trichlorovinyl, and the like. The alkyl substituents represented by R can have either branched- or straight-chain spatial configuration.

The amides (II, supra) are well-known in the literature or may be produced by various known means for example by the reaction of acryloyl chloride with the appropriate amine, or by the reaction of acrylonitrile with an appropriate alcohol or olefin. It is necessary that only the mono substituted amide be used, (i.e., that a hydrogen remain on the amide nitrogen) because a N,N-di substituted amide cannot be oxidatively ring closed to the desired isothiazolone.

As sources of sulfur and halogen the sulfur halides, (III, supra) preferably "sulfur monochloride", chemically $S_2Cl_2$, or sulfur dihalide, preferably sulfur dichloride, $SCl_2$ are used. From about 2 to about 4 moles of sulfur halide are required, with about 3 moles (per mole of acrylamide) preferred. To prepare the 4,5-dihalogen derivative (i.e., $X^1=X^2=$halo) as the major product, an organic amine base is necessary, such as pyridine or triethylamine, in molar amounts from about 0.2 to about 0.5 moles based on amide. If the organic base is omitted, the major product will be the 4-haloisothiazolone.

A reaction temperature of at least about 90° C. is required; a temperature in the range of from about 100° to about 130° C. is preferred. A reaction time of from 1 to 15 hours may be used. (With $SCl_2$, an excessively long reaction time will result in lower yields.) A number of solvents are suitable, as long as they are essentially unreactive to the reagents. Chlorobenzene, other ring-halogenated aromatics, ethylene dichloride (which will require pressure reaction equipment at the higher temperatures) and other halogenated alkanes are most suitable. Both batch conditions, where all ingredients are present at the start of the reaction, and gradual-addition conditions, wherein the amide (II) is added gradually to the sulfur halide (III), may be utilized.

The following examples illustrate this process; however, other materials will react in a similar manner to afford the desired products (I, supra).

EXPERIMENTAL

Gas chromatography was used to measure ratios of the 4,5-dihaloisothiazolone to the 4-haloisothiazolone. The specific compounds were identified by gas chromatography/mass spectrometry or with gas chromatography with addition of standards performed on a Varian 3700 gas chromatograph fitted with a Megabore DB-1 column (15M length, 1.5 micron film). Helium was used as carrier gas at a flow rate of 8 ml./min. A standard temperature program was used (100° C. isothermal for 2 minutes, followed by a 20° C./minute ramp to 290° C.). Identification of the 4,5-dichloro-2-cyclohexylisothiazolone was confirmed by high pressure liquid chromatography.

EXAMPLE I

Preparation of 4,5-Dichloro-2-cyclohexylisothiazolone (DCCHI) by Reaction of Cyclohexyl acrylamide (CHAA) with Sulfur monochloride (SM)

A 50-ml. flask was equipped with a magnetic stirrer, a means for introducing a slow flow of nitrogen gas, a reflux condenser, and a dropping funnel. The exit gases were scrubbed of hydrogen halide. This equipment was used for all preparative runs unless otherwise noted.

The reactions in Tables I-A and I-B were carried out in a batch mode. The solvent was chlorobenzene. MCCHI refers to 4-chloro- 2-cyclohexylisothiazolone. In Table I-A, the base was added dropwise to the CHAA/solvent/SM slurry; exotherms of 50° to 70° C. were noted. In Table I-B, the SM was added dropwise to the base/CHAA/solvent slurry, resulting in exotherms of 90°–110° C.

For analysis, an aliquot was treated with aqueous base to neutralize residual acids, and the organic layer analyzed directly, with addition of known amounts of DCCHI and MCCHI (or of comparable controls when other amines were used) for calibration.

TABLE I-A

| | CAA (mm) | S2Cl2 (mm) | Base | (mm) | Solv. (ml) | Time hrs | Temp °C. | Ratio, DCCHI/ MCCHI | DCCHI, yield (%) |
|---|---|---|---|---|---|---|---|---|---|
| (a) | 46 | 156 | Et3N | 26 | 18 | 18.5 | 120 | 8.9 | 32 |
| (b) | " | 137 | Et3N | 26 | 10 | 22 | 120 | 7.6 | 21 |
| (c) | " | 137 | Et3N | 26 | 10 | 4.5 | 125 | 8.1 | 27 |
| (d) | " | 91 | Et3N | 26 | 10 | 22 | 127 | — | — |
| (e) | " | 91 | Et3N | 26 | 10 | 6 | 123 | — | — |
| (f) | " | 91 | Et3N | 17 | 10 | 5.5 | 126 | — | — |
| (g) | " | 137 | — | — | 10 | 22 | 124 | 1.0 | — |

TABLE I-B

| | CAA (mm) | S2Cl2 (mm) | Base | (mm) | Solv. (ml) | Time hrs | Temp °C. | Ratio, DCCHI/ MCCHI | DCCHI, yield (%) |
|---|---|---|---|---|---|---|---|---|---|
| (a) | " | 156 | " | 26 | 18 | 2.5 | 124 | 7.3 | 18 |
| (b) | " | " | " | " | " | 19.5 | 125 | 10.4 | 26 (22)* |
| (c) | " | 137 | " | 46 | 10 | 22 | 124 | 3.0 | 3.6 |
| (d) | " | " | " | 26 | " | 3.5 | 143 | 4.3 | 9.2 |
| (e) | " | " | pyr | 23 | 10 | 3.75 | 123 | 4.9 | 26 |
| (f) | " | " | " | " | " | 17.25 | 125 | — | 29 |
| (g) | " | " | " | " | 16.25 | 120 | — | 27 | |

*Yield is also determined by diluting with methylene chloride quenching with ice/water, separating the organic layer, drying, removal of solvent under vacuum, extracting with hot isopropanol (leaving behind precipitated sulfur) evaporating, and analyzing by HPLC with suitable internal standards.

This example shows the direct conversion of CHAA to DCCHI using SM.

EXAMPLE 2

Preparation of 4,5-Dichloro-2-Cyclohexylisothiazolone (DCCHI) by Reaction of N-Cyclohexyl Acrylamide (CHAA) with Sulfur Dichloride (SD).

The reactions in Table II were carried out in a mode. The solvent was chlorobenzene. MCCHI refers to the 4-chloro- 2-cyclohexylisothiazolone. In all runs except the first two, the SD was added dropwise, resulting in exotherms to 95°–100° C. In the first run, all components were mixed directly; in the second run, the SD was added dropwise, but the temperature was not allowed to exceed 50° C. during the addition.

This example shows that SD may be used in place of SM for the direct conversion of CHAA to DCCHI.

TABLE II

| | CAA (mm) | SCl2 (mm) | Base | (mm) | Solvent (ml) | Time h | Temp °C. | Ratio, DCCHI/ MCCHI | yield (%) |
|---|---|---|---|---|---|---|---|---|---|
| (a) | 46 | 136 | Et3N | 26 | 10 | 22 | 120 | 0.9 | 3.1 |
| (b) | " | " | " | 26 | " | 5.6 | 100 | 5.8 | 16 |
| (c) | " | 91 | " | 17 | " | 6 | 110 | — | — |
| (d) | " | 136 | pyr | 23 | " | 6 | 115 | 6.3 | 19 |
| (e) | " | " | " | " | " | 6 | 110 | 4.6 | 26 |
| (f) | " | " | — | — | " | 6 | 124 | 0.6 | — |

EXAMPLE 3

Reaction of N-Cyclohexyl 2,3-Dichloropropionamide (DCPA) with Sulfuryl Chloride (SC) in Chlorobenzene The experimental technique of Example 2 was followed.

TABLE III

| | DCPA (mm) | S2Cl2 (mm) | Base | (mm) | Solvent (ml) | Time h | Temp °C. | DCCHI/ MCCHI | Ratio, yield (%) |
|---|---|---|---|---|---|---|---|---|---|
| (a) | 34 | 69 | " | 34 | " | 18.5 | 120 | 7.0 | 25 |
| (b) | 46 | 137 | " | 23 | " | 18.5 | " | 82 | 36 |

This example shows that DCPA may be used in place of CHAA to prepare DCCHI.

EXAMPLE 4

Low Yields from Reaction in Chlorobenzene 2,3-Dichloropropionamide (DCPA) with Sulfur Dichloride

TABLE IV

| | DCPA (mm) | SCl2 (mm) | Base | (mm) | Solv (ml) | Time h | Temp °C. | DCCHI/ MCCHI | Ratio, yield (%) |
|---|---|---|---|---|---|---|---|---|---|
| (a) | 46 | 91 | pyr | 15 | 10 | 19.5 | 115 | 20 | — |
| (b) | 40 | 80 | " | 20 | " | 22 | 110 | 18 | 8.7 |

Considerable DCPA remained at the end of the reaction.

EXAMPLE 5

Reaction of N-Octylacrylamide with SM

N-Octyl acrylamide (8.4 g; 0.046 moles) was mixed with triethylamine (26 g; 0.026 moles) and 18 ml. of chlorobenzene. To the mixture was added dropwise SM (0.156 moles); exotherming to about 100° C. was observed. The reactants were held for 19 hours at 125° C.

A yield of 22% of 4,5-dichloro-2-N-octylisothiazolone was obtained.

EXAMPLE 6

Reaction of 2-Chloro-N-cyclohexylacrylamide with SM in Chlorobenzene 2,3-Dichloro-N-cyclohexylpropionamide (DCPA, 0.046 moles) was converted to N-cyclohexyl- 2-chloroacrylamide in situ by reaction with 1.4 equivalents of pyridine by the following sequence: reaction with 1 equivalent of pyridine for 2 hours at 90° C., 20 hours at 105° C., followed by addition of 0.4 equivalents of pyridine and reaction at 120° C. for two hours. The mixture was cooled, and treated with chlorobenzene and SM as in Example 5. After 4 hours at 115° C., a 20% of yield of 4,5-dichloro-2-cycylohexylisothiazolone was achieved with minimal quantities of the 4-monochloro compound (ratio DCCHI/MCCHI=60).

The reaction shows that the 2-chloro acrylamide may be used in place of the CHAA.

EXAMPLE 7

Reaction of Cyclohexyl 3-Chloropropionamide (CCPA) with SM in Chlorobenzene

CCPA (4.6 ml. ) SM (15.6 ml.) and triethyl amine in 35 ml. of chlorobenzene were reacted at 120°-130° C. for several hours.

| Reaction time, hrs. | Ratio, DDCHI/MCCHI | Yield, DCCHI |
|---|---|---|
| 4.5 | 2.2 | 6 |

-continued

| Reaction time, hrs. | Ratio, DDCHI/MCCHI | Yield, DCCHI |
|---|---|---|
| 47 | 3.7 | 11 |

What is claimed is:

1. A process for preparing haloisothiazolones of the formula

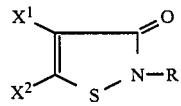

wherein
$X^1$ is halo;
$X^2$ is hydrogen or halo;
R is alkyl of 1 to 18 carbon atoms, alkenyl or alkynyl of 2 to 18 carbon atoms, cycloalkyl of 3 to 12 carbon atoms, aralkyl of up to 10 carbon atoms, or aryl of up to 10 carbon atoms; which comprises reacting an amide of the formula:

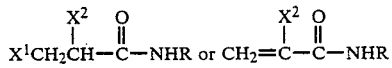

wherein $x^1$, $X^2$ and R are as defined above, with a sulfur-halogen compound or formula $(S)_m(halo)_n$ where m and n are integers of 1 or 2, optionally in the presence of an organic base.

2. The process of claim 1 where the reaction is carried out in a single kettle.

3. The process of claim 1 where X is hydrogen.

4. The process of claim 1 where X is chloro.

5. The process of claim 1 where R is selected from $C_1$-$C_8$ alkyl, cyclohexyl and n-octyl.

6. The process of claim 1 where the reaction is conducted with from about two to about four equivalents of the sulfur-halogen compound, (S)m(halo)n, where m and n are integers of 1 or 2, per equivalent of acrylamide.

7. The process of claim 1 where the reaction time is from one to fifteen hours and the reaction temperature is above 90° C.

8. The process of claim 1 where the sulfur-halogen compound is selected from $SCl_2$ or $S_2Cl_2$.

9. The process of claim 1 where an organic amine base is employed.

10. The process of claim 9 where the organic base is pyridine.

11. The process of claim 9 where the organic base is triethyl amine.

* * * * *